(12) United States Patent
Navarro Herrero et al.

(10) Patent No.: US 6,975,403 B2
(45) Date of Patent: Dec. 13, 2005

(54) ON-LINE METHOD AND EQUIPMENT FOR DETECTING, DETERMINING THE EVOLUTION AND QUANTIFYING A MICROBIAL BIOMASS AND OTHER SUBSTANCES THAT ABSORB LIGHT ALONG THE SPECTRUM DURING THE DEVELOPMENT OF BIOTECHNOLOGICAL PROCESSES

(75) Inventors: Jose Luis Navarro Herrero, Valencia (ES); Jesus Pico Marco, Valencia (ES); Jose Manuel Bruno Barcena, Burjassot (ES); Salvador Valles Albentosa, Burjassot (ES); Enrique Pico Marco, Valencia (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 10/757,717

(22) Filed: Jan. 14, 2004

(65) Prior Publication Data

US 2004/0227947 A1 Nov. 18, 2004

Related U.S. Application Data

(63) Continuation of application No. PCT/ES02/00355, filed on Jul. 16, 2002.

(30) Foreign Application Priority Data

Jul. 17, 2001 (ES) .......................................... 200101757

(51) Int. Cl.$^7$ .............................................. G01N 21/59
(52) U.S. Cl. ...................................................... 356/435
(58) Field of Search ................................ 356/433–436, 356/321

(56) References Cited

U.S. PATENT DOCUMENTS

| | | | | |
|---|---|---|---|---|
| 2,594,514 A | * | 4/1952 | Sweet | 356/434 |
| 3,489,906 A | * | 1/1970 | Beer | 356/435 |
| 3,674,370 A | * | 7/1972 | Jonsson | 356/435 |
| 4,037,972 A | * | 7/1977 | Pross | 356/435 |
| 5,699,156 A | * | 12/1997 | Carver | 356/319 |

* cited by examiner

Primary Examiner—Richard A. Rosenberger
(74) Attorney, Agent, or Firm—Klauber & Jackson

(57) ABSTRACT

The invention relates to a method comprising passing a first variable intensity light beam across a first test-tube (3) wherein the substance (1) to be controlled is circulating. Subsequently, a second fixed-intensity light beam is passed across a second test-tube (4) with a reference sample. The intensities of both beams are compared once they have crossed over the test tubes and the intensity of the first beam is varied so that said intensities are equal. The parameter of interest in the first test tube is calculated by means of signal processing which causes the first beam to vary.

12 Claims, 4 Drawing Sheets

ON-LINE METHOD AND EQUIPMENT FOR DETECTING, DETERMINING THE EVOLUTION AND QUANTIFYING A MICROBIAL BIOMASS AND OTHER SUBSTANCES THAT ABSORB LIGHT ALONG THE SPECTRUM DURING THE DEVELOPMENT OF BIOTECHNOLOGICAL PROCESSES

The present application is a Continuation of co-pending PCT Application No. PCT/ES02/00355, filed Jul. 16, 2002, which in turn, claims priority from Spanish Application Ser. No. 200101757, filed Jul. 17, 2001. Applicants claim the benefits of 35 U.S.C. §120 as to the PCT application and priority under 35 U.S.C. §119 as to said Spanish application, and the entire disclosures of both applications are incorporated herein by reference in their entireties.

OBJECT OF THE INVENTION

The present invention describes a system and a methodology for the on-line determination of the concentration of biomass and/or products contained in the culture medium. This is accomplished starting with the measurement of the optical absorption at wavelengths within the visible or infrared spectrum. This method makes it possible to obtain the real-time biomass concentration of different types of microorganisms and some by-products under different conditions within a wide range of values.

BACKGROUND OF THE INVENTION

In the field of biological process engineering, different commercial sensors or electrodes are currently available for detecting mainly physicochemical parameters such as temperature, pH, redox potential, dissolved oxygen and some ions. These elements record data, and most thereof control the parameters during one of the individual stages of which a specific biotechnological process is comprised. Thanks to this type of elements, it is possible, for example, in different types of industrial fermentation, to take measurements reflecting the status of any certain component during the microorganism culture process, which is especially important for scientists and operators in order to perform proper in-process control.

In most fermenting and in some separation processes, a proper control of the process dynamics is required, for which purpose estimating and determining the evolution of the concentration of a certain component contained in the fermenting medium is especially important. By means of a simple measurement, it must be possible to determine or estimate the amount of catalyst or by-product present in the culture medium. The concentration of the component in question may be modified in a controlled manner provided that it be possible to instantaneously detect the element in question and, therefore, that the proper detectors, in other words, transducers affording the possibility of converting the concentration of a certain parameter into an electrical signal, be available.

Different procedures for determining components in the fermenting medium are current state-of-the art, although the main microbiological problem which has become more acute over the course of time lies in this type of procedures being highly costly in terms of the time and material involved.

Conventionally, the measurement of the concentration of the substances present in the culture medium is made using different analytical techniques (dry weight measurement, spectroscopy, chromatography, etc.) on a sample of the medium taken from the bioreactor. This technique entails the drawback of a delay in obtaining the results (which can be significant in relation to the growth dynamics of the microorganism) and the small number of samples during the fermenting process.

The techniques utilized for the biomass concentration measurement are as follows:

Dry weight measurement: The liquid medium is separated from the solid (which is comprised mainly of microorganisms), the dry extract then being weighed. This is the most reliable and accurate measurement of the quantity of biomass per unit of volume, but it entails the drawback of not being possible to measure continuously and of the lag in the obtaining of the data.

Measurement of the optical density or absorbance to a wavelength. According to Beer's law, the absorption of monochromatic light by a medium is proportional to the concentration of substances which absorb the energy at that wavelength suspended in a medium transparent to that radiation, which affords the possibility of estimating the concentration of cellular microorganisms or other substances.

$$A = \log(P_o/P) = \epsilon * b * c$$

Where:
A: Absorbance of the sample
Po: Intensity of the light source
P: Intensity of the beam after passing through the sample
$\epsilon$: Specific absortivity
b: Thickness of the sample
c: Concentration of the absorbing substance in the sample This method can be used for the on-line measurement of the concentration by using a probe inserted into the bioreactor or by means of the continuous recirculation of the medium through the measuring device. Beer's law is only valid for low biomass concentrations. However, a relationship does exist (although non-linear) between the biomass concentration and the absorbance to media and high concentrations. In order for the measurement to be useful, there must be no significant absorption of other substances in the medium to the wavelength selected for making the measurement. Air bubbles or other solids present in the medium may interfere with the measurement.

Measurement of the stirring power: Some microorganisms (such as fungi) modify the apparent viscosity of the medium in terms of the total biomass present therein. This phenomenon may be utilized for making an estimate of the quantity of biomass in the medium by means of the measurement of the intensity consumed by the motor that moves the stirring blades and the angular speed thereof.

Measurement of the capacitance of the medium: When subjected to an electrical field, microorganisms may act as dipoles. If the culture medium is used as a dielectric between the plates of two electrodes and a sine current (0.1–1 MHz) is applied, the resulting capacitance is a function of the concentration of viable cells existing between the plates of the electrodes. This method is used in different sensors available on the market.

Research has been conducted related to documents of patents having to do with the present invention, such as:
JP-63015140 Turbidity sensor
U.S. Pat. No. 5,446,544 Turbidimeter
EP-0,590,487 Device for turbidity measurement in aqueous media U.S. Pat. No. 5,828,458 Turbidity sensor EP-0,869,350 Turbidity measuring system U.S. Pat. No. 3,962,041 Method and apparatus for measuring the opacity of fluids U.S. Pat. No. 4,893,935 Apparatus and method for optical density measurements of biomass processes U.S. Pat. No. 3,714,445 apparatus for optical measurements of microbial cultures U.S. Pat. No. 3,727,066 Probe photometer with fluid sensing device U.S. Pat. No. 3,819,278 Turbidity measuring device with means for preventing the formation of bubbles After analyzing these documents, it is our understanding that none thereof foregoes the present invention.

The measurement of the biomass and/or of some of the products is important, given that it affords the possibility of calculating the mass balances in the method, is necessary as a point of reference for calculating the specific rates at which the substrate is consumed and the product is generated, is an indicator of the kinetic evolution of the developing cells, in addition to being decisive for control purpose. For the purpose of achieving this objective, some sensors and methods have been devised over recent decades for estimating the biomass concentration in the reactor. Most of them make the estimate of the biomass through the use of optical principles, although there are estimating methods based on the dielectric properties of the biomass and on the changes in density of the cultured media, as has been discussed at an earlier point hereinabove.

DESCRIPTION OF THE INVENTION

To achieve the objectives, the invention consists of an on-line method and equipment for detecting, determining the evolution and quantifying a microbial biomass and other substances that absorb light along the spectrum during the development of biotechnological processes.

The method is based on the measurement of the light intensity absorbed by a culture medium at a specific wavelength, in other words, the measurement of the optical density. As an innovation, according to the invention, said method consists of the following:

A first light beam of variable intensity and pre-set frequency range is made to pass through a first test-tube through which the substance to be controlled is running.

A second light beam of fixed intensity and the aforementioned pre-set spectrum is made to pass through a second test-tube containing a reference sample of the substance to be controlled.

The intensity of the first and second beams is continuously compared after passing through the respective test-tubes.

The intensity of the first beam is continuously varied so that the intensities of the first and second beams will be identical in the aforementioned comparison.

The corresponding electrical signal is processed, which determines the aforementioned continuous variation for the continuous real-time calculation of the biomass concentration or parameter of interest in the first test-tube.

The calculation of the biomass concentration or parameter of interest can be made based on a calibration pattern which is a model correlating the values of the aforementioned electrical signal with the biomass concentration or parameter of interest, the concentration of all of the other products of interest being estimated based on this model by way of a suitable observer.

The aforementioned model can be obtained by means of a suitable calibration test affording the possibility of comparing the measurement provided by the sensor for different samples of which the concentrations are known.

The equipment corresponding to the method described above comprises:

Means of pumping and circulating the substance to be controlled from a bioreactor to a first test-tube.

A second test-tube in which a reference sample of the culture medium present in the bioreactor is placed.

Means of emitting light of a variable intensity and pre-set range of frequencies that are applied to the first test-tube.

Means of emitting light of a constant intensity and the same frequency range mentioned in the immediately preceding paragraph hereinabove, which are applied to the second test-tube.

Means of sensing the light which passes through the first test-tube.

Means of sensing the light which passes through the second test-tube.

Means of comparing the two signals corresponding to the light intensities sensed by the above-mentioned sensing means.

Means for adjusting the output signal, such that by means of the modification of the power applied to the light-emitting means, the difference between the two output signals of the sensing means will be nil or, equivalently, that the output signal of the aforementioned means of comparison will be nil.

Means for varying the power applied to the means of emitting light of variable intensity as a function of the output signal of the means of adjustment.

Means for sensing and remote transmission of the instant value of the signal which is being applied to the means of emitting variable intensity light.

And means for processing the output signals of the aforementioned sensing and transmission means, and for calculating (in terms of the output signal and of a calibration pattern) the parameter of interest of the aforementioned substance.

According to a preferred embodiment of the invention, the light-emitting means consist of LED diodes which emit at wavelengths within the light spectrum and which provide for absorbance values sensed by the sensing means within the 0.1 to 40 optical density range.

The equipment of the invention may incorporate means for eliminating any possible cases of interference caused by gas bubbles or other particles. Said means of eliminating any possible cases of interference may consist of an air valve located downstream from the first test-tube, or may also consist of the use of a filtering algorithm integrated into the system processing means.

The aforementioned pumping and circulating means of the system shall preferably consist of a hydraulic pump with the suitable pipage.

According to the aforementioned preferred embodiment, the above-mentioned test-tubes are of a sturdy material with a low absorption index for light at the wavelengths emitted by the light-emitting means. Additionally, in the example embodiment of the invention, the aforementioned test-tubes are located in one same compartment, such that the temperature inside the same will be the same for the purpose of preventing any drift effects due to temperature changes.

The aforementioned means of adjustment may consist of a PI controller.

The means for varying the power may consist of a voltage-intensity converter.

The aforementioned means of processing and calculation may have some functional blocks that include a reading data block followed by a filtering block and an estimating block which calculates the concentration of substances of interest based on a mathematical model, this estimating block being connected to a recalibration block and to a results display block. In addition thereto, an optional control block can be incorporated, affording the possibility of obtaining the instant value of the flow of substrate to the bioreactor, thus optimizing the production of biomass or substance of interest.

The equipment can be recalibrated on-line by means of the modification of the internal calibration model (estimating block) based on the comparison of the result provided by the instrument and the measurement obtained based on an occasional analysis of a sample taken from the bioreactor.

In the following, in order to facilitate a better comprehension of this description and comprising an integral part thereof, some figures are provided, in which, for non-limiting purposes of illustration, the object of the invention is shown.

DESCRIPTION OF ONE EMBODIMENT OF THE INVENTION

A description is provided in following of one embodiment of the invention, making reference to the numbering used in the Figures.

Figure 1:
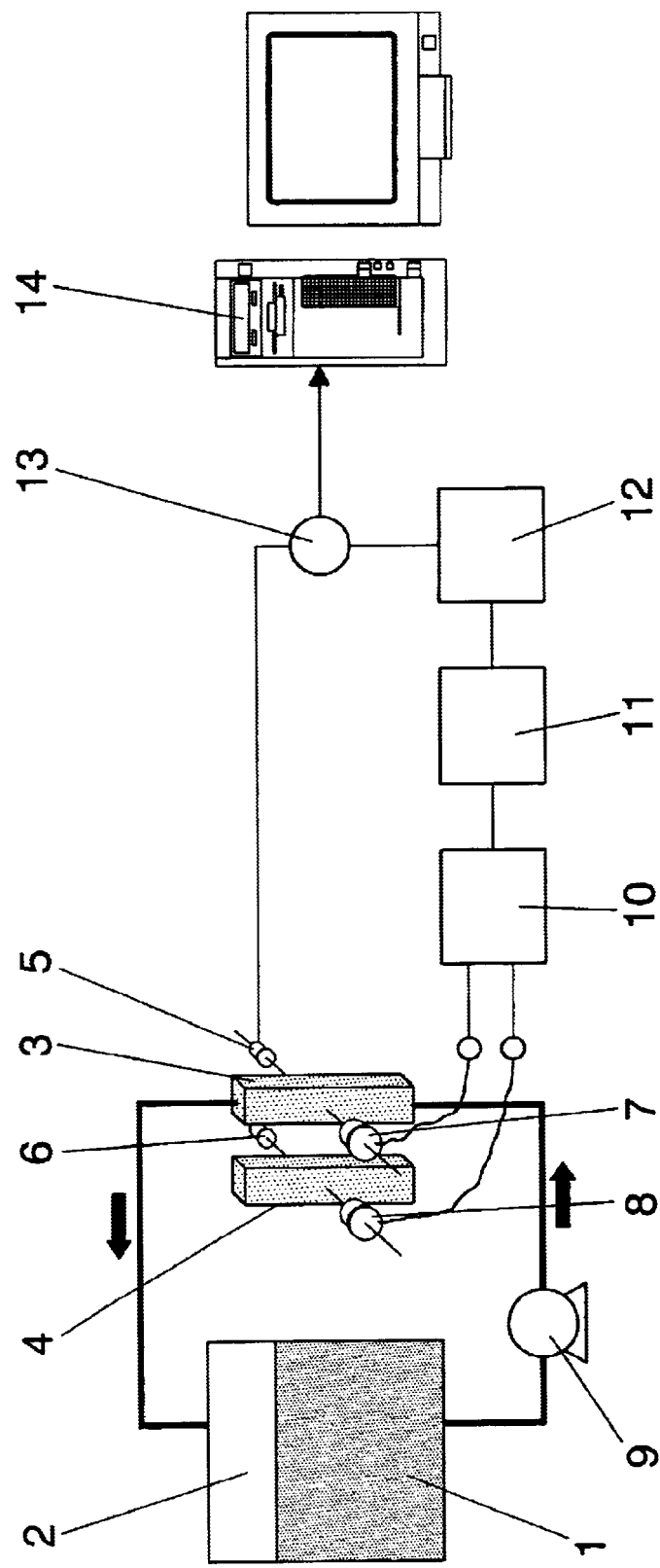
FIG. 1. Illustrates the elements comprising the equipment which employs the method of the present invention according to one embodiment thereof.

Thus, the equipment shown in FIG. 1 avails of some means for pumping and circulating the substance (1) to be controlled from a bioreactor or similar (2) to a first test-tube (3), said means being comprised of a hydraulic pump (9) and the necessary pipage.

There is also a second test-tube (4) in which there is a static control sample of the substance (1) to be controlled.

Some means of emitting light of variable intensity (5) and of a pre-set frequency range act on the test-tube (3), while some means of emitting light of a constant intensity (6) within the same aforementioned frequency range act on test-tube 4. Behind the light-emitting means (5,6) and the test-tubes (3,4) are means for sensing light (7,8), the signals of which are transmitted to some means of comparison (10), the output of which is transmitted to some means of adjustment (11) which may consist of a PI controller.

The regulator output (11) is transmitted to a voltage-intensity converter (12) which modifies the intensity of the light-emitting means (5) such that said variation in the intensity determines the difference between the two output signals of the sensing means (7,8) being nil.

FIG. 1 also shows some means for sensing and transmitting (13) the instant value of the signal which is being applied to the means (5), which may consist of a current sensor.

Lastly, FIG. 1 includes means of processing and calculation (14) to which the signal picked up by means 13 is transmitted. These means of processing and calculation (14) act as a function of the signal transmitted thereto and of a pattern for the calibration of the parameter of interest of the substance (1), such that the signal applied to the light-emitting means (5) is converted into an indication of the instant variation of biomass in test-tube 3.

In this example, the light-emitting means (5,6) consist of LED diodes which emit at wavelengths within the visible or infrared spectrum and which allows the possibility of absorbance values sensed by means 7 and 8 between 0.1 and 40 in optic density. These means (7,8) consist of silicon photodiodes.

In the present example, it has been anticipated to avail of means for eliminating any possible interference caused by gas bubbles or other particles by means of a filtering algorithm integrated into the means of processing and calculation (14).

The test-tubes (3,4) are of a sturdy material having a low light absorption index at the wavelengths emitted by means 5 and 6.

Additionally, test-tubes (3,4) are located in one some compartment, such that the temperature in these test-tubes will the be same such that there will be no drift effects due to temperature changes.

Figure 2:
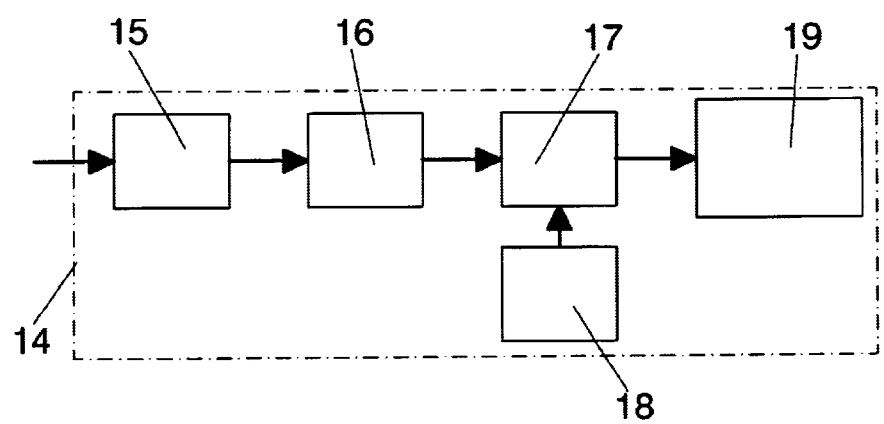
FIG. 2. Provides a functional block diagram of the processing and calculation means included in FIG. 1 above.

The functional blocks of the means of processing and calculation (14) are shown in FIG. 2, showing a reading data block (15), the mission of which is that of reading the signal transmitted to means 14 at a pre-set frequency. This block (15) is connected to a filtering block (16), the mission of which is that of eliminating and offsetting, by means of a suitable algorithm, the variations caused by the bubbles present in the medium. In turn, block 16 is connected to an estimating block (17) which calculates the concentration of the substances of interest based on a dynamic mathematical model of the behavior of the microorganisms in the bioreactor (2). This block (17) is connected to a recalibration block (18), the mission of which is that of recalculating the parameters of the model used according to available additional information, as well as the values of the concentrations sporadically obtained by analytical means within a quality control policy (samples every eight or twelve hours). Additionally, block 17 is connected to a results display block (19). The diagram in FIG. 2 could optionally be expanded by means of a control block, allowing the possibility of instantaneously obtaining the value of the flow of substrate to the bioreactor (2), such as to make it possible to optimize, according to a previously-set criterion, the production of biomass or protein.

Figure 3:
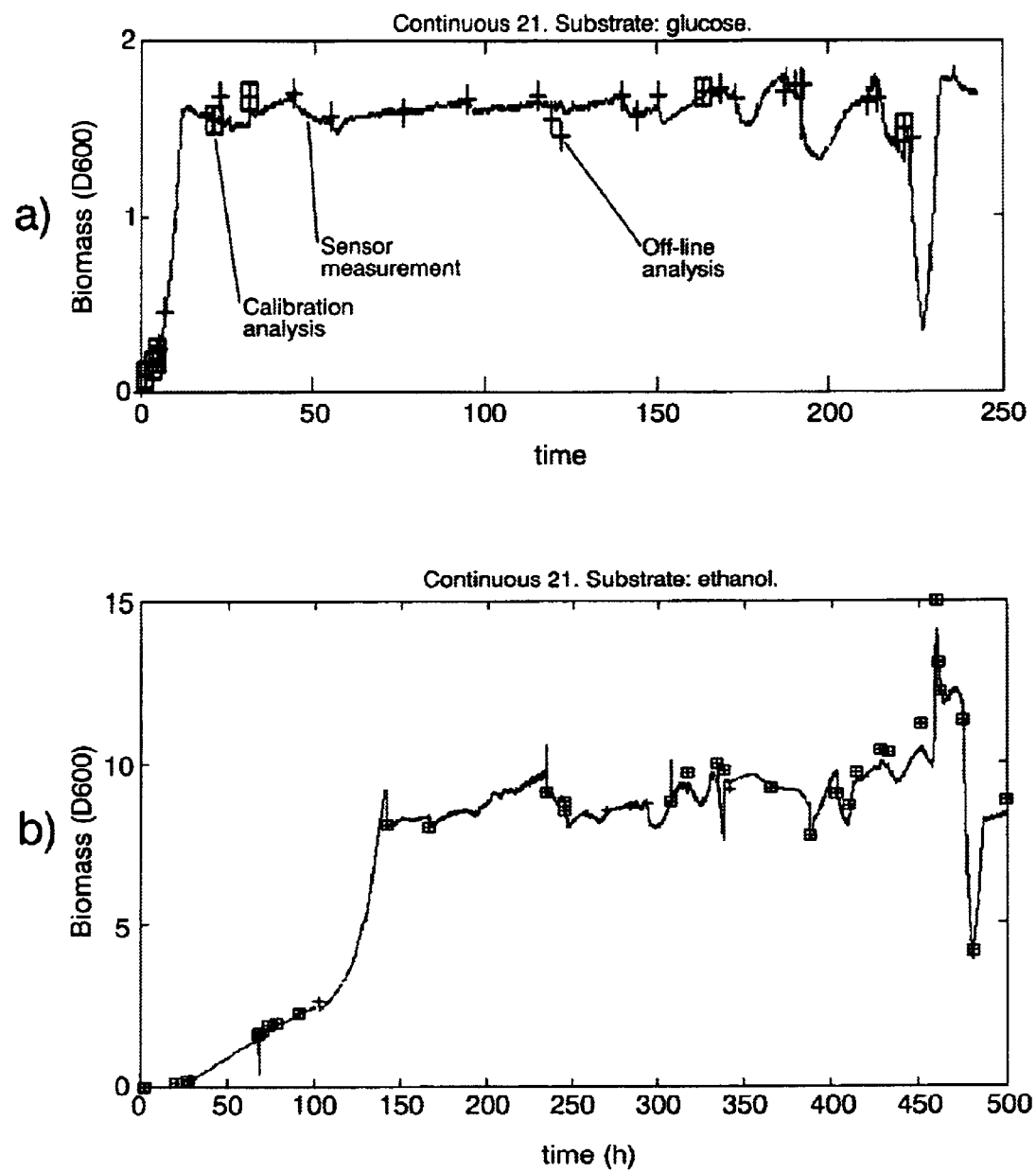
FIG. 3. Provides the real-time measurement graphics of the concentration of the T73 strain of the *saccharomicees cerevisae* yeast in different culture situations, the graphic lettered (a) corresponding to the concentration of biomass in a culture with glucose and that lettered (b) to the culture made with ethanol.
Figure 4:
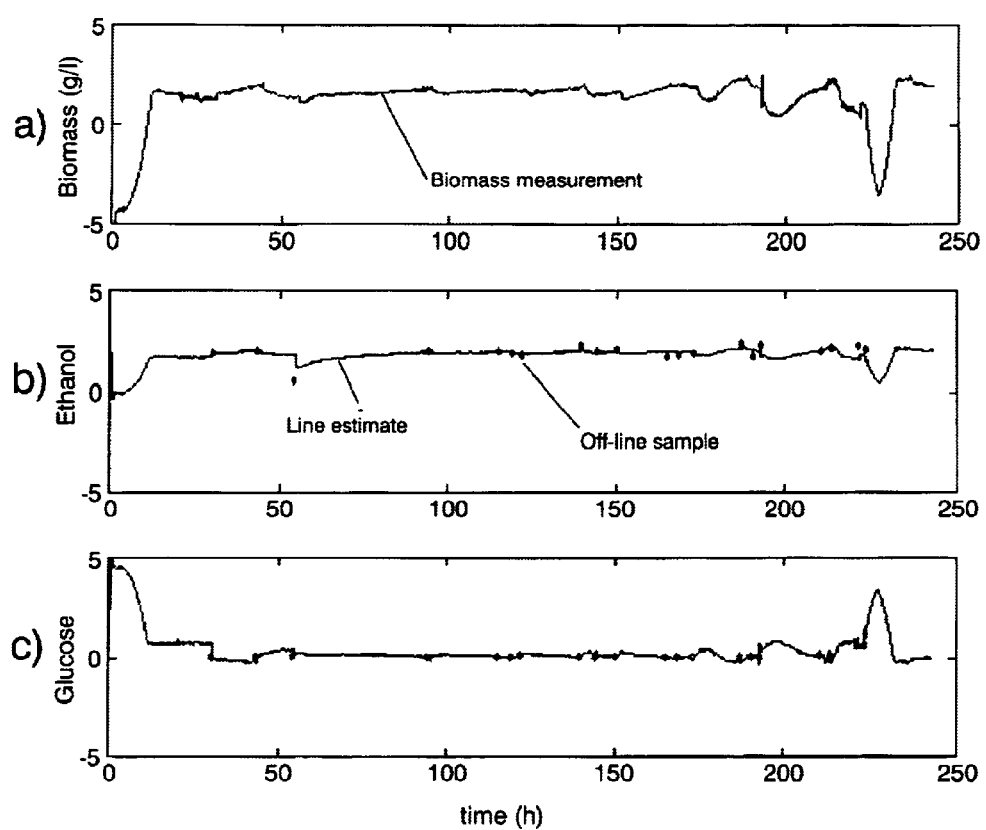
FIG. 4. Samples the graphics of the evolution of the concentration of biomass (a), of ethanol (b) and of glucose (c) obtained from an asymptotic observer (sensor software) complemented with a Kalman filter for the case of glucose feeding.

The graphics shown in FIGS. 3 and 4 show actual cases of utilization of the system of the invention, measuring, in real time, the concentration of *saccharomicees cerevisae* in a continuous experiment. In FIG. 3, the Y axes show the absorbance of the medium (DO600), whilst the X axes show the time in hours. In FIG. 4, the coordinate axes show the concentration of compounds in gr/l In the example corresponding to said graphics, the concentration of the T73 strain of the *sacchromicees cerevisae* yeast (SC) is made in real time. An amber-colored LED has been used as the light-emitting element, said LED emitting a 600 nm wavelength. As the sensing element, a silicon photodiode has been used. Apart from this, the electronic device has been built using operational amplifiers. As a computing element, a personal computer with a data acquisition card has been used.

Algorithms for the filtering of the signal in order to eliminate the effect of the bubbles and to estimate the yeast concentration based on the measurement of the corresponding sensor have also been programmed. The results are those shown in FIGS. 3 and 4.

The graphics show different situations, corresponding, in the case of FIG. 3, to the concentration of biomass in the culture according to the calibration pattern. The graphic (a) in FIG. 3 corresponds to the concentration when the culture is fed with glucose, while graphic (b) is related to a situation similar to the preceding one, but feeding the culture with ethanol.

Apart from the above, as a continuation of the application, a sensor software has been designed for the concentrations of glucose and ethanol in the T73 culture for case (a) (glucose-fed) based on an asymptotic observer complemented with a Kalman filter, the results for which are shown in FIG. 4.

The method corresponding to the equipment in FIG. 1 is inferred from the description which has been provided of said equipment, additionally perfectly fitting the method description provided in the previous "Description of the Invention" section, as a result of which, it is not considered necessary to repeat said description of the method in this section.

What is claimed is:

1. Equipment for detecting, determining the evolution and quantifying a microbial mass and other substances that absorb light along the spectrum during the development of biotechnological processes, comprising:

means for pumping and circulating (9) the substance to be controlled from a bioreactor or similar source (2) to a first test-tube (3), a second test-tube (4) in which a static control sample of the substance (1) to be controlled is placed, means for emitting light of a variable intensity (5) and pre-set range of frequencies that are applied to the first test-tube (3), means of for emitting light of a constant intensity (6) and in the same said frequency range, which are applied to the second test-tube (4), means for sensing (7) the light which passes through the first test-tube (3) and providing a first signal in accordance with the light intensity sensed, means for sensing (8) the light which passes through the second test-tube and providing a second signal in accordance with the light intensity sensed (4), means for comparing (10) the two said first and second signals corresponding to the light intensities sensed by the said sensing means and providing an output signal in accordance with the intensity difference (7,8), means for adjusting (11) the said output signal, such that by means of the modification of the power applied to the light-emitting means (5), the difference between the two said signals of the sensing means (7,8) will be nil or, equivalently, that the output signal of the means of comparison (10) will be nil, means for varying the power (12) applied to the means of emitting light of variable intensity (5) in terms of the output signal of the means of adjustment (11), means for sensing and transmitting (13) the instant value of the signal which is being applied to the means of emitting variable intensity light (5), and means for processing (14) the output signals of the aforementioned sensing and transmitting means (13), and for calculating in terms of the output signal and of a calibration pattern the parameter of interest of the aforementioned said substance (1).

2. Equipment for detecting, determining the evolution and quantifying a microbial mass and other substances that absorb light along the spectrum during the development of biotechnological processes, as per claim 1, wherein said light-emitting means (5,6) consist of LED diodes which emit at wavelengths within the visible or infrared spectrum and the light-sensing means (7,8) consist of silicon photodiodes.

3. Equipment for detecting, determining the evolution and quantifying a microbial mass and other substances that absorb light along the spectrum during the development of biotechnological processes as per claim 1, comprising means for eliminating any possible cases of interference caused by gas bubbles or other particles.

4. Equipment for detecting, determining the evolution and quantifying a microbial mass and other substances that absorb light along the spectrum during the development of biotechnological processes, as per claim 3, wherein said means of eliminating any interference consist of an air valve which is located downstream from the first test-tube (3).

5. Equipment for detecting, determining the evolution and quantifying a microbial mass and other substances that absorb light along the spectrum during the development of biotechnological processes, as per claim 3 wherein said means of eliminating any possible cases of interference consist of a filtering algorithm which is integrated into the processing means (14).

6. Equipment for detecting, determining the evolution and quantifying a microbial mass and other substances that absorb light along the spectrum during the development of biotechnological processes, as per claim 1, wherein said pumping and circulating means (9) consist of a hydraulic pump with a suitable pipage.

7. Equipment for detecting, determining the evolution and quantifying a microbial mass and other substances that absorb light along the spectrum during the development of biotechnological processes, as per claim 1, wherein said test-tubes (3,4) are of a sturdy materials with a low light absorption index at the wavelengths emitted by the light-emitting means (5,6).

8. Equipment for detecting, determining the evolution and quantifying a microbial mass and other substances that absorb light along the spectrum during the development of biotechnological processes, as per claim 1, wherein the two test-tubes (3,4) are located in one same compartment, such that the temperature inside these test-tubes will be the same for the purpose of preventing any drift effects due to temperature changes.

9. Equipment for detecting, determining the evolution and quantifying a microbial mass and other substances that absorb light along the spectrum during the development of biotechnological processes, as per claim 1, wherein the means of adjustment (11) consist of a PI controller adjuster.

10. Equipment for detecting, determining the evolution and quantifying a microbial mass and other substances that absorb light along the spectrum during the development of biotechnological processes, as per claim 1, wherein means of processing and calculation (14) are subject to being recalibrated by means of the comparison of the results provided thereby and the occasional analysis of the aforementioned substance (1).

11. Equipment for detecting, determining the evolution and quantifying a microbial mass and other substances that absorb light along the spectrum during the development of biotechnological processes, as per claim 1, wherein the means of varying the power (12) consist of a voltage-intensity converter.

12. Equipment for detecting, determining the evolution and quantifying a microbial mass and other substances that absorb light along the spectrum during the development of biotechnological processes, as per claim 1, wherein the aforementioned means of processing and calculation (14) functionally include a reading data block (15) followed by the filtering block (16) and an estimating block (17) which calculates the concentration of substances of interest based on a mathematical model and which is connected to a recalibration block (18) and to a results display block (19), it also being possible for an optional control block to be incorporated, affording the possibility of obtaining the instant value of the flow of the substrate to the bioreactor (2), thus optimizing the production of biomass or substance of interest.

* * * * *